United States Patent
Kershman et al.

(10) Patent No.: US 10,188,628 B1
(45) Date of Patent: Jan. 29, 2019

(54) **RELEASE COMPOSITION FOR DERIVATIVES OF *CANNABACEAE***

(71) Applicants: Alvin Kershman, Chesterfield, MO (US); Jeff Shear, Bonita Springs, FL (US)

(72) Inventors: Alvin Kershman, Chesterfield, MO (US); Jeff Shear, Bonita Springs, FL (US)

(*) Notice: Subject to any disclaimer, the term of this patent is extended or adjusted under 35 U.S.C. 154(b) by 0 days.

(21) Appl. No.: 15/793,848

(22) Filed: Oct. 25, 2017

Related U.S. Application Data

(60) Provisional application No. 62/413,796, filed on Oct. 27, 2016.

(51) Int. Cl.
| | | |
|---|---|---|
| *A61K 31/352* | (2006.01) | |
| *A61K 9/00* | (2006.01) | |
| *A61K 47/14* | (2017.01) | |
| *A61K 47/10* | (2017.01) | |

(52) U.S. Cl.
CPC .......... *A61K 31/352* (2013.01); *A61K 9/0014* (2013.01); *A61K 47/10* (2013.01); *A61K 47/14* (2013.01)

(58) Field of Classification Search
CPC ...... A61K 31/352; A61K 9/004; A61K 47/10; A61K 47/14

USPC ......................................................... 514/454
See application file for complete search history.

(56) References Cited

U.S. PATENT DOCUMENTS

| | | |
|---|---|---|
| 6,946,150 B2 | 9/2005 | Whittle |
| 2003/0229027 A1 | 12/2003 | Eissens |
| 2007/0104741 A1 | 5/2007 | Murty |
| 2010/0008985 A1 | 1/2010 | Pellikaan |
| 2011/0092583 A1 | 4/2011 | Murty |
| 2014/0166027 A1 | 6/2014 | Fuisz |
| 2014/0166028 A1 | 6/2014 | Fuisz |

FOREIGN PATENT DOCUMENTS

| | | |
|---|---|---|
| WO | 2004016246 | 2/2004 |

*Primary Examiner* — Raymond J Henley, III
(74) *Attorney, Agent, or Firm* — CreatiVenture Law; Linda L. Lewis; Dennis Donahue

(57) ABSTRACT

A release lotion for delivering *Cannabaceae* derivatives, including THC made by combining an aqueous phase at least one humectant; wherein the humectant is present in the aqueous phase in the range of from about 1 to 99 wt. %; and an oil phase comprising *Cannabaceae* derivatives and at least one surfactant, wherein the surfactant is present in the oil phase in the range of from about 1 to 99 wt. %, and wherein the aqueous phase is added to the oil phase in a weight ratio of about 3:1 to 49:1 using low to medium shear mixing, and wherein the lotion is hydrophobic and has release properties.

20 Claims, No Drawings

RELEASE COMPOSITION FOR DERIVATIVES OF *CANNABACEAE*

CROSS-REFERENCE TO RELATED APPLICATIONS

This application claims the benefit of provisional patent application 62/413,796 filed on Oct. 27, 2017 which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

This invention relates to release formulations for administering derivatives of *Cannabaceae* in a release composition form.

Related Art

Cannabinoids are compounds derived from the *Cannabis sativa* plant, which is part of the larger group of plants known as *Cannabaceae*, also commonly known as marijuana. Derivatives of *Cannabaceae* and more specifically, the plant *Cannabis sativa* contain more than 400 chemicals and approximately 60 cannabinoids. These include cannabidiol and cannabinol. The most active chemical compound of the naturally occurring cannabinoids is tetrahydrocannabinol (THC), particularly $\Delta^9$-THC.

Currently, $\Delta^9$-tetrahydrocannabinol, also known as Dronabinol, is available commercially in Marinol® soft gelatin capsules which have been approved by the Food and Drug Administration (FDA) for the control of nausea and vomiting associated with chemotherapy and for appetite stimulation of AIDS patients suffering from the wasting syndrome. The $\Delta^9$-tetrahydrocannabinol shows other biological activities, which lend themselves to possible therapeutic applications, such as in the treatment of glaucoma, migraine headaches, spasticity, anxiety, analgesia, and drug addiction.

In Marinol®, $\Delta^9$-THC is dissolved in sesame oil and encapsulated in gelatin capsules for oral administration. After oral administration, Dronabinol has an onset of action of approximately 0.5 to 1 hour, with a peak effect at 2-4 hours. The duration of action for psychoactive effects is 4-6 hours, but the appetite stimulant effect may continue for 24 hours or longer after administration. The maximal plasma levels after oral dosing of 20 mg $\Delta^9$-THC in a sesame oil formulation are around 10 ng/ml.

At the present time, some cancer patients manage to obtain prescriptions for marijuana in order to alleviate pain as well as nausea and vomiting due to chemotherapy. This latter situation arises due to poor or partial response from oral therapy, which often requires oral administration two to three times a day to obtain equivalent acute psychological and physiological effects obtained from smoking marijuana.

When administered orally, $\Delta^9$-THC or Dronabinol is almost completely absorbed (90-95%) after a single oral dose. However, due to the combined effect of first pass hepatic metabolism and high lipid solubility, only about 10-20% of an administered dose reaches systemic circulation with highly variable maximal concentrations. It has been found that fasting or food deprivation may decrease the rate of absorption of $\Delta^9$-THC from the sesame oil capsules currently available in the market. Previous studies have reported that another limitation of orally administered $\Delta^9$-THC is the large inter-subject variability in absorption.

Other postulated mechanisms for the biopharmaceutical anomalies can be attributed to the physical-chemical properties of $\Delta^9$-THC. This compound is highly lipophilic, essentially water insoluble, and potentially acid labile within the stomach. This compound is also sensitive to environmental storage and stress conditions. For instance, this compound is thermolabile and photolabile, and long-term storage can lead to a cumulative decrease in $\Delta^9$-THC content by an oxidation reaction forming cannabinol (CBN).

It is well known that in mammals certain areas of the alimentary canal have a venous drainage, which does not involve a first pass through the liver. The avoidance of the first pass effect is the rationale for the use of rectal, buccal, nasal, and sublingual formulations. A $\Delta^9$-THC and cannabidiol combination has been formulated as a buccal spray. Some of the disadvantages associated with nasal, sublingual and buccal routes of administration are that these routes may cause pain or reflex sneezing and, in extreme cases, may cause irritation and damage to the nasal mucosa. Sublingual formulations may stimulate the flow of saliva, making it difficult for patients to avoid swallowing the dosage when substantial amounts of saliva are produced.

Both sublingual and buccal formulations depend on the efficient transfer of medicament from a hydrophilic vehicle to the mucous membrane of the sublingual or buccal mucosa. Transfer of medicament through the interstices between or through epithelial cells is governed principally by the lipid solubility of the medicament. When a drug is water insoluble as in the case with cannabinoids, this presents a further barrier to absorption from the sublingual area.

Dronabinol or $\Delta^9$-THC belongs to Class II (low aqueous solubility and high permeability) of the biopharmaceutical classification system (BCS). A self-emulsifying (SEDDS) lipid based delivery system may enhance the dissolution of a drug system in an aqueous environment. Patents demonstrating the potential use of SEDDS or lipid delivery systems for lipophilic drugs include U.S. Pat. No. 9,265,724, which discloses a SEDDS delivery system for $\Delta^9$-THC and is hereby incorporated by reference.

None of the prior art systems, above, disclose the present invention of a release system for *Cannabaceae* derivatives.

SUMMARY OF THE INVENTION

The present invention relates to a release composition for administering *Cannabaceae* derivatives comprising a lotion made by combining an aqueous phase comprising at least one humectant, and wherein the at least one humectant is present in the aqueous phase in the range of from 1 to 99 wt. %. and an oil phase comprising THC, optionally at least one additional oil, and at least one surfactant, wherein the surfactant is present in the oil in the range of from about 1 to 99 wt. %. The aqueous phase is added to the oil phase in a weight ratio of about 3:1 to 49:1 using low to medium shear mixing to provide the lotion. The lotion is hydrophobic and can control the release of *Cannabaceae* derivatives.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

"*Cannabaceae* derivatives release properties" is defined as the properties of the lotion, to release the derivatives. Preferably, there is a rapid (short) first effect time, a rapid (short) peak effect time, and a long end effect time.

The oil phase is prepared from a hydrophobic solution or mixture containing at least one surfactant and the *Cannabaceae* derivatives. The preferred *Cannabaceae* derivatives include CBD and THC. The surfactant is preferably a non-water soluble surfactant having an HLB number of less than 4, and includes emulsifiers. Examples of suitable surfactants include oleic acid, acetylated monoglycerides, glycerol dioleate, sorbitan tristearate, glycerol monoleate, acetylated monoglycerides, lecithin and various combinations of these. A preferred surfactant is commercially sold as ATMOS®-300K, and is a combination of mono- and diglycerides made from edible food sources and propylene glycol.

The surfactant is present in the oil phase in the amount of about 1 to 99%. An optional oil suitable for the oil phase is typically liquid or semi-solid at room temperature, and is compatible with wounds, the epidermis and the oral cavity. One or more additional oils comprise terpenes or other plant oils with aromatic, flavor, or chemical profiles to enhance the lotion fragrance, flavor, or biological effect. Such oils include plant oils, such as vegetable oil, corn oil, canola oil, coconut oil, castor oil or olive oil; essential oils, such as peppermint oil, lavender oil or cinnamon oil; and animal fats such as tallow and lard. The oils include petroleum distillates, such as petrolatum and mineral oil. Mixtures of oils are also contemplated in the present invention. In one embodiment, the oil phase is present in the composition in the range of from about 0.1 to 50 wt %.

Preferred *Cannabaceae* derivatives include, but are not limited, to Delta(9)-tetrahydrocannabinol, cannabidiol, cannabichromene, cannabinol, cabbabigerol, tetrahydrocannabivarin, cannabidivarin, Delta(8)-tetrahydrocannabinol, tetrahydrocannabinol acid, cannabidiol acid, cannabigerol acid, cannabigerovarin, cannabinovarin, and tetrahydrocannabivarin acid or combinations thereof. Sources of THC include THC extracted in the form of plant oils using various solvents including $CO_2$ and butane, and include Super (77.7%), Distillate (85%), Vape (60%), and Crude (63%) oils. These sources of THC are a mixture of oils that include flavonoids, terpenoids and cannabidiol. The derivatives of *Cannabaceae* that include THC, CBD, CBN, CBG, CBC, THCV as well as other current and yet to be isolated cannabinoids are present in the lotion in the range of about 0.1 to about 25.0 wt %.

The aqueous phase contains at least one humectant. Suitable humectants include, but are not limited to glycerine, lactic acid, polyols, propylene glycol, high fructose corn syrup, and sorbitol. A preferred combination of humectants is glycerin and sorbitol. A preferred form of sorbitol is non-crystallizing liquid sorbitol (70 wt. % sorbitol in water). The combination of glycerin and non-crystalizing liquid sorbitol provides additional stability to the composition. The ratio of glycerin to non-crystalizing liquid sorbitol is from 1:2 to 3:1. Most preferably, the ratio is about 5:2. The at least one humectant is present in the aqueous phase from 1 to 100 wt. %. The amount of at least one humectant in the lotion composition is from about 1 to 99 wt. %. Preferably, the amount of humectant in the lotion composition is from about 40 to 80 wt. %. More preferably, the amount of humectant in the lotion composition is from about 60 to 80 wt. %.

A preferred *Cannabaceae* derivatives release composition comprises a lotion comprising:
  from about 50 to 99 wt. % humectant;
  from about 1 to 50 wt. % water;
  from about 0.001 to 25.00 wt. % *Cannabaceae* derivatives;
  from about 0 to 25 wt. % additional oil;
  from about 25 to 1 wt. % surfactant;
  wherein the lotion is hydrophobic and has release properties.

Other additives suitable for the present invention include, but are not limited to colorings and flavorings, such as peppermint oil.

The claimed composition is typically prepared using a planetary or counter rotating type mixer preferably having a rubber lined mixing bowl equipped with a rubber coated wire whip stirring device. The rubber surface helps the mixing of the two phases, but plastic or an abraded or roughened surface will also work. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the composition is conducted in 2 steps:

Step 1 produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 3:1 to 49:1), this initial process step is concluded.

Step 2 begins with the seed batch of Step 1, at the desired final weight ratio of aqueous phase to oil phase. The volume of seed material needed for Step 2 is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

In another embodiment of the invention, the lotion is prepared as is disclosed in Table 1 below.

Lotion Composition

TABLE 1

| Run # | 63-10A | 63-10B | 63-11A | 63-12A | 63-12B | 63-15B | Control 63-16A | 63-16B | 63-17A | 63-17B |
|---|---|---|---|---|---|---|---|---|---|---|
| Ingredient/wt. % | | | | | | | | | | |
| THC (Super 77.7%)[1] | 5.742 | | | | | | | | | |
| THC (Distillate 85%)[1] | | 6.28 | | | | | | | | |
| THC (Vape 60%)[1] | | | 4.434 | 4.434 | 4.434 | | 29.35 | 5.869 | 14.93 | 2.935 |
| THC (Crude 63%)[1] | | | | | | 4.656 | | | | |
| Other Cannabis oils[1] | 1.648 | 1.11 | 2.956 | 2.956 | 2.956 | 2.734 | 19.56 | 3.913 | 9.96 | 7.956 |
| Atmos-300 Surfactant | 7.39 | 7.39 | 7.39 | 3.695 | | 7.39 | 48.91 | 9.782 | 24.89 | 4.891 |
| Soy Lecithin Surfactant | | | | 3.695 | 7.39 | | | | | |
| Peppermint Oil | 0.33 | 0.33 | 0.33 | 0.33 | 0.33 | 0.33 | 2.18 | 0.436 | 0.22 | 0.218 |
| Sorbitol[2] humectant | 29.71 | 29.71 | 29.71 | 29.71 | 29.71 | 28.71 | | 28.00 | 17.50 | 31.5 |
| Glycerol humectant | 42.32 | 42.32 | 42.32 | 42.32 | 42.32 | 42.32 | | 39.88 | 24.92 | 44.86 |
| Water[2] | 12.96 | 12.96 | 12.96 | 12.96 | 12.96 | 12.97 | 0 | 12.12 | 7.58 | 13.64 |
| Aqueous/Oil Ratio | 85/15 | 85/15 | 85/15 | 85/15 | 85/15 | 85/15 | NA | 80/20 | 50/50 | 90/10 |
| Total | 100.0 | 100.0 | 100.0 | 100.0 | 100.0 | 100.0 | 100.0 | 100.0 | 100.0 | 100.0 |

[1]THC from various sources are reported as a combination of THC and Other Cannabis oils. They reported separately for comparison purposes.
[2]A non-crystallizing liquid sorbitol (70 wt. % sorbitol in water) which is reported separately as Sorbitol humectant and Water.

Method of Preparing the Lotion Shown in Table 1

A. Preparing Oil Phase

1. Warm the THC oil to 26.7° C.
2. Add Atmos® 300K, peppermint oil, and optionally, the lecithin.
3. Mix well and set aside.

B. Preparing the Aqueous Phase

1. Mix the sorbitol solution non-crystallizing liquid sorbitol (70 wt. % sorbitol in water) and glycerin together and warm to 43.33° C.
2. Remove heat source.

C. Forming the Lotion

1. Using a 5 quart lab Hobart type planetary lab/kitchen mixer with a rubber or plastic lined wire whip and rubber or plastic lined bowl add 40 g of oil phase and stir on #2 (low shear) setting.
2. Slowly add approx. 200-300 g aqueous phase with mixing.
3. Add remainder of the oil phase to the bowl. Slowly add remainder of the aqueous phase to the bowl with mixing. Scrape the sides of the bowl with a spatula to ensure thorough mixing.
4. Increase the speed to #4 for 10 minutes more, making sure to scrape the sides of the bowl occasionally. After 10 minutes, the lotion is prepared.

The lotion of Examples from Table 1, above, is viscous, pourable, non-water dispersible and has THC release properties.

Testing the Lotion

The lotion was administered to a human or animal by applying to a mucous membrane of the human or animal a dose of a lotion made by the process of combining:

A) an aqueous phase comprising an aqueous solution or suspension containing and at least one humectant; wherein the at least one humectant is present in the aqueous phase in the range of from about 0.1 to 99 wt. %, and B) an oil phase comprising at least one surfactant and Cannabaceae derivatives, and optionally at least one additional oil, wherein the at least one surfactant is present in the oil phase in the range of from about 1 to 99 wt. %;

wherein the aqueous phase is added to the oil phase in a weight ratio of about 3:1 to 49:1; wherein the aqueous phase is added to oil phase using low to medium shear mixing to provide the lotion; and wherein the lotion is hydrophobic and has THC release properties.

The desired release properties include a rapid first effect time, which is the time at which the first effects of the Cannabaceae derivatives are felt after administering the composition, as reported by the user. The first effect time is less than about 20 minutes. Preferably the first effect time is less than about 15 minutes, and most preferably the first effect time is less than about 12 minutes. A second desired release property is a rapid peak effect time, which is the peak time after the composition is administered, as reported by the user. The peak time is less than 60 minutes, and preferably less than about 50 minutes. A third desired release property is a long time until the effect ends. The end time is the time after the composition is administered that the effect ends, as reported by the user. The end time is greater than about 60 minutes. Preferably the end time is greater than about 90 minutes, and most preferably the end time is greater than about 120 minutes.

In a series of trials with human volunteers, the lotion was administered in a variety of ways. The first was a method of syringing the dosage into the mouth, and massaging the lotion into the gums using a finger. The second method was placing the dosage under the upper lip and massaging the lotion into the upper gum using the lip. Unless otherwise stated the first method of syringing into the mouth was used.

Once the lotion was administered, it was absorbed into the mucous membrane. No residue was removed from the mucous membrane after administration.

As shown in Table 2, four different sources of THC were tested on human volunteers. The lotion dosages were to deliver 10 mg THC and were administered by syringing into the mouth the lotion and massaging the lotion into the gums. The ratio of oil/aqueous was 85/15. The time data was average among those tested and is given in minutes.

TABLE 2

| Formula | Dosage | Time 1st effect | Time peak | Time wane | Time end |
|---|---|---|---|---|---|
| 63-10 B | 10 mg | 14.25 | 47.38 | 98.00 | 134.86 |
| 63-10 A | 10 mg | 18.88 | 44.75 | 68.13 | 90.50 |
| 63-11 A | 10 mg | 10.18 | 49.09 | 86.45 | 113.09 |
| 63-15 B | 10 mg | 13.10 | 43.30 | 90.10 | 101.00 |

The dosage giving the quickest onset time was 63-11A, which was used as a standard of comparison for the next tests.

As shown Table 3, changing the method of application had a great impact on the Time to first Effect, the Peak Time, and the Time to End. For the first application, the 10 mg lotions were syringed into the mouth and massaged into the gums. For the second application, the lotion was placed under the top lip and massaged into the gums. The second application showed a more rapid first effect and lasted longer.

TABLE 3

| Formula | Dosage | Application | Time 1st effect | Time peak | Time wane | Time end |
|---|---|---|---|---|---|---|
| 63-11 A | 10 mg | Into mouth | 10.18 | 49.09 | 86.45 | 113.09 |
| 63-11 A | 10 mg | Under front lip | 8.00 | 28.83 | 83.83 | 135.50 |

As shown in Table 4, varying the dosage from 10 mg to 5 mg THC shortens the experience but does not change the time to first effect.

TABLE 4

| Formula | Dosage | Time to 1st effect | Time to peak | Time to wane | Time to end |
|---|---|---|---|---|---|
| 63-11 A | 10 mg | 10.18 | 49.09 | 86.45 | 113.09 |
| 63-11 A | 5 mg | 10.67 | 34.50 | 50.67 | 74.83 |

As shown in Table 5, Control 63-16A, which does not have an aqueous phase, performed poorly compared to the present invention embodied in 63-17A and 63-11 A.

TABLE 5

| Formula | Ratio of Aqueous/Oil | Dosage | Time to 1st effect | Time to peak | Time to wane | Time to end |
|---|---|---|---|---|---|---|
| Control 63-16 A | 0/100 | 10 mg | 14.00 | 29.64 | 51.91 | 71.36 |
| 63-17 A | 50/50 | 10 mg | 14.44 | 39.78 | 86.56 | 104.88 |
| 63-11 A | 85/15 | 10 mg | 10.18 | 49.09 | 86.45 | 113.09 |

As shown in Table 6, a variety of formula were tested. The ratio of aqueous/oil phases varied between 80/20 to 90/10, and the dosage varied from 5 mg to 10 mg.

TABLE 6

| Formula | Dosage | Time to 1st effect | Time to peak | Time to wane | Time to end | Ratio of Aqueous/Oil |
|---|---|---|---|---|---|---|
| 63-11A | 10 mg | 10.18 | 49.09 | 86.45 | 113.09 | 85/15 |
| 63-16B | 10 mg | 11.50 | 52.50 | 131.75 | 188.75 | 80/20 |
| 63-17B | 5 mg | 12.50 | 36.17 | 55.40 | 93.40 | 90/10 |

In Table 7, the surfactant was varied from all Atmos-300 to all Lecithin, and to a combination of Atmost-300 and lecithin. The use of lecithin appears to extend the time of effect, but to delay time to first effect.

TABLE 7

| Formula | Surfactant | Time to 1st effect | Time to peak | Time to wane | Time to end |
|---|---|---|---|---|---|
| 63-11A | Atmos-300 | 10.18 | 49.09 | 86.45 | 113.09 |
| 63-12AD | Atmos-300/Lecithin | 10.90 | 46.44 | 85.89 | 135.00 |
| 63-12BE | Lecithin | 16.25 | 68.25 | 116.75 | 150.88 |

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A release composition for *Cannabaceae* derivatives comprising a lotion made by the process of combining:
   A) an aqueous phase comprising an aqueous solution or suspension containing and at least one humectant; wherein the at least one humectant is present in the aqueous phase in the range of from about 0.1 to 99 wt. %, and
   B) an oil phase comprising at least one surfactant and the *Cannabaceae* derivatives, and optionally at least one additional oil, wherein the at least one surfactant is present in the oil phase in the range of from about 1 to 99 wt. %;
   wherein the *Cannabaceae* derivative comprises a compound selected from the group consisting of tetrahydrocannabinol, cannabidiol, cannabichromene, cannabinol, cabbabigerol, tetrahydrocannabivarin, cannabidivarin, tetrahydrocannabinol acid, cannabidiol acid, cannabigerol acid, cannabigerovarin, cannabinovarin, and tetrahydrocannabivarin acid and combinations thereof;

wherein the aqueous phase is added to the oil phase in a weight ratio of about 3:1 to 49:1;

wherein the aqueous phase is added to oil phase using low to medium shear mixing to provide the lotion; and wherein the lotion is hydrophobic and has release properties.

2. The composition of claim 1, wherein the surfactant has an HLB of less than 4.

3. The composition of claim 1, wherein the surfactant is selected from the group consisting of oleic acid, acetylated monoglycerides, glycerol dioleate, sorbitan tristearate, glycerol monoleate, propylene glycol monoglyceride, propylene glycol diglyceride, lecithin and combinations thereof.

4. The composition of claim 1, wherein the humectant is present in the lotion from about 40 wt. % to about 99 wt. %.

5. The composition of claim 1, wherein the humectant is present in the lotion composition from about 40 wt. % to about 80 wt. %.

6. The composition of claim 1, wherein the humectant is selected from the group consisting of glycerine, lactic acid, polyols, propylene glycol, corn syrup, and sorbitol.

7. The composition of claim 6, wherein the sorbitol is non-crystallizing liquid sorbitol solution.

8. The composition of claim 1, wherein the humectant is a combination of glycerin and non-crystalizing liquid sorbital.

9. The composition of claim 1 wherein the *Cannabaceae* derivatives comprise Delta(9)-tetrahydrocannabinol.

10. A method of preparing a *Cannabaceae* derivatives release composition comprising a lotion made by the method:
A) mixing to form an aqueous solution or suspension comprising at least one humectant, wherein the at least one humectant is present in the aqueous phase in the range of from about 0.1 to 99 wt. %, and
B) mixing to form an oil phase comprising at least one surfactant, the *Cannabaceae* derivatives and optionally at least one additional oil, wherein the at least one surfactant is present in the oil phase in the range of from about 1 to 99 wt. %; and
C) adding the aqueous phase to the oil phase in a ratio of about 3:1 to 49:1 using low medium shear mixing to provide the lotion;
wherein the *Cannabaceae* derivative comprises a compound selected from the group consisting of tetrahydrocannabinol, cannabidiol, cannabichromene, cannabinol, cabbabigerol, tetrahydrocannabivarin, cannabidivarin, tetrahydrocannabinol acid, cannabidiol acid, cannabigerol acid, cannabigerovarin, cannabinovarin, and tetrahydrocannabivarin acid and combinations thereof; and wherein the lotion is hydrophobic and has release properties.

11. The composition of claim 10, wherein the humectant is present in the lotion from about 40 wt % to about 99 wt %.

12. The composition of claim 10, wherein the humectant is a combination of glycerine and non-crystalizing liquid sorbital solution.

13. A method of administering *Cannabaceae* derivatives to a human or animal comprising applying to a mucous membrane of the human or animal a dose of a lotion made by the process of combining:
A) an aqueous phase comprising an aqueous solution or suspension containing and at least one humectant; wherein the at least one humectant is present in the aqueous phase in the range of from about 0.1 to 99 wt. %, and
B) an oil phase comprising at least one surfactant, the *Cannabaceae* derivatives, and optionally at least one additional oil, wherein the at least one surfactant is present in the oil phase in the range of from about 1 to 99 wt. %;
wherein the aqueous phase is added to the oil phase in a weight ratio of about 3:1 to 49:1; wherein the aqueous phase is added to oil phase using low to medium shear mixing to provide the lotion;
wherein the *Cannabaceae* derivative comprises a compound selected from the group consisting of tetrahydrocannabinol, cannabidiol, cannabichromene, cannabinol, cabbabigerol, tetrahydrocannabivarin, cannabidivarin, tetrahydrocannabinol acid, cannabidiol acid, cannabigerol acid, cannabigerovarin, cannabinovarin, and tetrahydrocannabivarin acid and combinations thereof; and
wherein the lotion is hydrophobic and has release properties.

14. The method of claim 13, wherein the surfactant is selected from the group consisting of oleic acid, acetylated monoglycerides, glycerol dioleate, sorbitan tristearate, glycerol monoleate, propylene glycol monoglyceride, propylene glycol diglyceride, lecithin and combinations thereof.

15. The method of claim 13, wherein the humectant is present in the composition from about 50 wt % to about 99 wt %.

16. The method of claim 13, wherein the humectant is selected from the group consisting of glycerine, lactic acid, polyols, propylene glycol, corn syrup, and sorbitol.

17. The method of claim 16, wherein the sorbitol is non-crystallizing liquid sorbitol.

18. The method of claim 15, wherein the humectant is a combination of glycerine and sorbital.

19. The method of claim 13, wherein the lotion is applied to the gums of a human or animal.

20. The method of claim 19, wherein the lotion is squirted onto the gums of a human or animal and massaged into the gums.

* * * * *